US007254850B2

United States Patent
Newkirk et al.

(10) Patent No.: US 7,254,850 B2
(45) Date of Patent: *Aug. 14, 2007

(54) RADIAL ARM SYSTEM FOR PATIENT CARE EQUIPMENT

(75) Inventors: David C Newkirk, Lawrenceburg, IN (US); Michael E Cerimele, Indianapolis, IN (US); Mark A. Graham, Springboro, OH (US); Christian H Reinke, York, SC (US); Jonathan D Turner, Dillsboro, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/422,365

(22) Filed: Jun. 6, 2006

(65) Prior Publication Data

US 2006/0207025 A1    Sep. 21, 2006

Related U.S. Application Data

(63) Continuation of application No. 10/802,287, filed on Mar. 17, 2004, now Pat. No. 7,065,811.

(60) Provisional application No. 60/510,756, filed on Oct. 13, 2003, provisional application No. 60/455,621, filed on Mar. 18, 2003.

(51) Int. Cl.
  *A61G 7/00*    (2006.01)
  *B65H 75/34*   (2006.01)
  *F16L 3/22*    (2006.01)
(52) U.S. Cl. .................... 5/600; 5/658; 137/355.16
(58) Field of Classification Search ............... 5/600, 5/658, 81.1 R, 503.1, 904, 905; 248/278.1, 248/282.1, 284.1; 52/27, 36.4; 137/355.16
See application file for complete search history.

(56) References Cited

U.S. PATENT DOCUMENTS

| 860,303 A | 7/1907 | Jones ................. 248/278.1 |
| 1,686,341 A | 10/1928 | Nathanson ........... 248/284.1 |
| 1,915,985 A | 6/1933 | Edwards ............. 340/286.07 |
| 2,208,945 A | 7/1940 | Miller ..................... 297/170 |
| 2,439,009 A | 4/1948 | Kujawski ................. 403/56 |
| 2,547,532 A | 4/1951 | Mendelsohn ....... 248/292.11 |
| 2,607,881 A | 8/1952 | Anderson ................ 362/144 |
| 3,012,781 A | 12/1961 | Nelson ..................... 473/430 |
| 3,030,128 A | 4/1962 | Versen ...................... 285/185 |
| 3,112,968 A | 12/1963 | Cotton et al. ............ 312/248 |
| 3,213,877 A | 10/1965 | May et al. ............ 137/355.16 |
| 3,243,497 A | 3/1966 | Kendall et al. ............ 174/61 |
| 3,272,928 A | 9/1966 | Hainzelin ................. 191/1 R |
| 3,358,957 A | 12/1967 | Lindenmuth .......... 248/279.1 |
| 3,431,937 A | 3/1969 | Hettlinger et al. ..... 137/355.16 |
| 3,556,455 A | 1/1971 | Storm et al. .............. 248/333 |
| 3,609,211 A | 9/1971 | Van Herk .................. 174/49 |

(Continued)

FOREIGN PATENT DOCUMENTS

DE    92 04 321.6 U1    5/1992

(Continued)

*Primary Examiner*—Robert G. Santos
(74) *Attorney, Agent, or Firm*—Barnes & Thornburg LLP

(57) ABSTRACT

A system for supporting patient care equipment alongside a patient support is provided. In one embodiment, the system includes a plurality of arms supported by a support structure. The arms may be pivoted to either side of the patient support. The arms may be stored in a console. At least one of the arms may carry service conduits that provide medical air, oxygen, vacuum, nitrogen, nitrous oxide, or electricity.

20 Claims, 15 Drawing Sheets

U.S. PATENT DOCUMENTS

| | | | | |
|---|---|---|---|---|
| 3,662,981 A | 5/1972 | Hogrebe | ............... | 248/278.1 |
| 3,757,363 A | 9/1973 | Langlais | ............... | 5/503.1 |
| 3,820,752 A | 6/1974 | Oram | ............... | 248/284.1 |
| 3,889,914 A | 6/1975 | Torme | ............... | 248/445 |
| 3,977,645 A | 8/1976 | Deely | ............... | 248/284 |
| 4,023,757 A | 5/1977 | Allard et al. | ............... | 248/70 |
| 4,032,775 A | 6/1977 | Bobrick et al. | ............... | 362/426 |
| 4,080,530 A | 3/1978 | Krogsrud | ............... | 362/402 |
| 4,094,484 A | 6/1978 | Galione | ............... | 248/162.1 |
| 4,107,769 A | 8/1978 | Saluja | ............... | 362/402 |
| 4,160,536 A | 7/1979 | Krogsrud | ............... | 248/280.11 |
| 4,165,530 A | 8/1979 | Sowden | ............... | 362/401 |
| 4,166,602 A | 9/1979 | Nilsen et al. | ............... | 248/280.11 |
| 4,183,489 A | 1/1980 | Copher et al. | ............... | 248/278.1 |
| 4,208,028 A | 6/1980 | Brown et al. | ............... | 224/185 |
| 4,266,747 A | 5/1981 | Souder, Jr. et al. | ............... | 248/280.11 |
| D261,804 S | 11/1981 | Foster et al. | ............... | D24/185 |
| 4,353,411 A | 10/1982 | Harter et al. | ............... | 165/48.1 |
| 4,410,158 A | 10/1983 | Maffei | ............... | 248/214 |
| 4,452,499 A | 6/1984 | Verburg | ............... | 312/209 |
| 4,453,687 A | 6/1984 | Sweere | ............... | 248/183.3 |
| 4,453,695 A | 6/1984 | Sennott et al. | ............... | 248/660 |
| 4,465,255 A | 8/1984 | Hill | ............... | 248/441.1 |
| 4,475,322 A | 10/1984 | Russo et al. | ............... | 52/27 |
| 4,494,177 A | 1/1985 | Matthews | ............... | 362/402 |
| 4,523,732 A | 6/1985 | Biber et al. | ............... | 248/123.11 |
| 4,562,987 A | 1/1986 | Leeds et al. | ............... | 248/278.1 |
| 4,591,124 A | 5/1986 | Hellenbrand et al. | ............... | 248/447.2 |
| 4,610,118 A | 9/1986 | Fullenkamp | ............... | 52/240 |
| 4,687,167 A | 8/1987 | Skalka et al. | ............... | 248/126 |
| 4,744,019 A | 5/1988 | Krogsrud | ............... | 362/402 |
| 4,770,384 A | 9/1988 | Kuwazima et al. | ............... | 248/281.11 |
| 4,795,122 A | 1/1989 | Petre | ............... | 248/317 |
| 4,801,116 A | 1/1989 | Biette et al. | ............... | 307/112 |
| 4,817,903 A | 4/1989 | Braehler et al. | ............... | 248/419 |
| 4,836,478 A | 6/1989 | Sweere | ............... | 248/279.1 |
| 4,844,387 A | 7/1989 | Sorgi et al. | ............... | 108/5 |
| 4,846,434 A | 7/1989 | Krogsrud | ............... | 248/284.1 |
| 4,856,741 A | 8/1989 | Schaefer | ............... | 248/122.1 |
| 4,879,798 A | 11/1989 | Petre | ............... | 29/434 |
| 4,901,967 A | 2/1990 | Petre | ............... | 248/327 |
| 4,945,592 A | 8/1990 | Sims et al. | ............... | 5/658 |
| 4,993,683 A | 2/1991 | Kreuzer | ............... | 248/639 |
| 4,997,155 A | 3/1991 | Reuter et al. | ............... | 248/278.1 |
| 5,026,017 A | 6/1991 | Kreuzer | ............... | 248/324 |
| 5,072,906 A | 12/1991 | Foster | ............... | 248/122.1 |
| 5,100,091 A | 3/1992 | Pollak | ............... | 248/278.1 |
| 5,107,636 A | 4/1992 | Schindele et al. | ............... | 52/27 |
| 5,108,063 A | 4/1992 | Koerber, Sr. et al. | ............... | 248/284.1 |
| 5,108,064 A | 4/1992 | Kreuzer | ............... | 248/327 |
| 5,113,897 A | 5/1992 | Kummerfeld et al. | ............... | 137/357 |
| 5,186,337 A | 2/1993 | Foster et al. | ............... | 211/26 |
| 5,284,255 A | 2/1994 | Foster et al. | ............... | 211/26 |
| 5,288,277 A | 2/1994 | Kummerfeld | ............... | 474/198 |
| 5,299,338 A | 4/1994 | Foster | ............... | 5/658 |
| 5,306,109 A | 4/1994 | Kreuzer et al. | ............... | 414/343 |
| 5,333,103 A | 7/1994 | Cvek | ............... | 362/413 |
| 5,340,072 A | 8/1994 | Halbirt | ............... | 248/279.1 |
| 5,348,260 A | 9/1994 | Acevedo | ............... | 248/280.11 |
| 5,377,371 A | 1/1995 | Foster | ............... | 5/503.1 |
| 5,398,359 A | 3/1995 | Foster | ............... | 5/658 |
| 5,421,548 A | 6/1995 | Bennett et al. | ............... | 248/129 |
| 5,452,807 A | 9/1995 | Foster et al. | ............... | 211/26 |
| 5,455,975 A | 10/1995 | Foster | ............... | 5/600 |
| 5,456,655 A | 10/1995 | Morris | ............... | 601/23 |
| 5,479,958 A | 1/1996 | Kummerfeld | ............... | 137/357 |
| 5,597,385 A | 1/1997 | Moerke | ............... | 96/416 |
| 5,603,496 A | 2/1997 | Rappaport | ............... | 473/487 |
| 5,618,090 A | 4/1997 | Montague et al. | ............... | 312/209 |
| 5,644,876 A | 7/1997 | Walker | ............... | 52/220.7 |
| 5,738,316 A | 4/1998 | Sweere et al. | ............... | 248/123.11 |
| 5,743,503 A | 4/1998 | Voeller et al. | ............... | 248/284.1 |
| 5,799,917 A | 9/1998 | Li | ............... | 248/284.1 |
| 5,826,846 A | 10/1998 | Buccieri et al. | ............... | 248/280.11 |
| 5,842,672 A | 12/1998 | Sweere et al. | ............... | 248/278.1 |
| 5,876,008 A | 3/1999 | Sweere et al. | ............... | 248/325 |
| 5,878,536 A | 3/1999 | Demmitt et al. | ............... | 52/36.4 |
| 5,895,886 A | 4/1999 | Beuster et al. | ............... | 174/48 |
| D412,161 S | 7/1999 | Theis et al. | ............... | D14/447 |
| 5,924,665 A | 7/1999 | Sweere et al. | ............... | 248/285.1 |
| D413,110 S | 8/1999 | Sweere et al. | ............... | D14/447 |
| 5,947,429 A | 9/1999 | Sweere et al. | ............... | 248/123.11 |
| 5,966,760 A | 10/1999 | Gallant et al. | ............... | 5/658 |
| 5,967,479 A | 10/1999 | Sweere et al. | ............... | 248/280.11 |
| 5,992,809 A | 11/1999 | Sweere et al. | ............... | 248/278.1 |
| D418,603 S | 1/2000 | Gallant | ............... | D24/185 |
| 6,045,596 A | 4/2000 | Holland, Jr. et al. | ............... | 55/385.2 |
| 6,095,468 A | 8/2000 | Chirico et al. | ............... | 248/282.1 |
| 6,146,158 A | 11/2000 | Peratoner et al. | ............... | 439/110 |
| 6,152,426 A | 11/2000 | Von Fange | ............... | 254/334 |
| 6,155,743 A | 12/2000 | Chen | ............... | 403/374.1 |
| 6,170,102 B1 | 1/2001 | Kreuzer | ............... | 5/601 |
| 6,179,260 B1 | 1/2001 | Ohanian | ............... | 248/229.16 |
| 6,201,983 B1 | 3/2001 | Haumann et al. | ............... | 600/407 |
| 6,213,481 B1 | 4/2001 | Marchese et al. | ............... | 280/35 |
| 6,231,526 B1 | 5/2001 | Taylor et al. | ............... | 600/587 |
| D443,365 S | 6/2001 | Walker | ............... | D24/232 |
| 6,256,935 B1 | 7/2001 | Walker | ............... | 52/27 |
| 6,269,594 B1 | 8/2001 | Walker | ............... | 52/27 |
| D452,573 S | 12/2001 | Walker | ............... | D24/232 |
| 6,343,601 B1 | 2/2002 | Kiske et al. | ............... | 128/203.12 |
| 6,349,436 B1 | 2/2002 | Kreuzer | ............... | 5/600 |
| 6,431,515 B1 | 8/2002 | Gampe et al. | ............... | 248/324 |
| 6,434,329 B1 | 8/2002 | Dube et al. | ............... | 396/14 |
| 6,471,363 B1 | 10/2002 | Howell et al. | ............... | 362/11 |
| 6,553,587 B1 | 4/2003 | Barker et al. | ............... | 5/600 |
| 6,639,623 B2 | 10/2003 | Howell et al. | ............... | 348/61 |
| 6,668,493 B1 | 12/2003 | Walker | ............... | 52/27 |
| 6,725,483 B2 | 4/2004 | Gallant et al. | ............... | 5/658 |
| 6,899,442 B2 | 5/2005 | Howell et al. | ............... | 362/147 |
| 7,040,057 B2* | 5/2006 | Gallant et al. | ............... | 52/36.1 |
| 7,065,811 B2* | 6/2006 | Newkirk et al. | ............... | 5/600 |
| 7,065,812 B2* | 6/2006 | Newkirk et al. | ............... | 5/600 |
| 7,073,765 B2* | 7/2006 | Newkirk | ............... | 248/647 |
| 7,097,145 B2* | 8/2006 | Turner | ............... | 248/281.11 |
| 2001/0030683 A1 | 10/2001 | Howell et al. | ............... | 348/61 |
| 2002/0015296 A1 | 2/2002 | Howell et al. | ............... | 362/11 |
| 2003/0014817 A1 | 1/2003 | Gallant et al. | ............... | 5/600 |
| 2003/0021107 A1 | 1/2003 | Howell et al. | ............... | 362/147 |
| 2004/0040086 A1 | 3/2004 | Eisenberg et al. | ............... | 5/81.1 R |
| 2004/0164220 A1 | 8/2004 | Newkirk | ............... | 248/647 |
| 2004/0188578 A1 | 9/2004 | Turner | ............... | 248/281.11 |
| 2004/0199996 A1 | 10/2004 | Newkirk et al. | ............... | 5/81.1 R |
| 2005/0000019 A1 | 1/2005 | Newkirk et al. | ............... | 5/600 |
| 2006/0043244 A1* | 3/2006 | Graham et al. | ............... | 248/161 |
| 2006/0207025 A1* | 9/2006 | Newkirk et al. | ............... | 5/600 |
| 2006/0207026 A1* | 9/2006 | Newkirk et al. | ............... | 5/600 |
| 2006/0226333 A1* | 10/2006 | Newkirk | ............... | 248/647 |
| 2006/0242763 A1* | 11/2006 | Graham et al. | ............... | 5/503.1 |

FOREIGN PATENT DOCUMENTS

| | | |
|---|---|---|
| DE | 29805019 U1 | 5/1998 |
| EP | 0 215 212 A | 3/1987 |
| EP | 0 257 299 A | 3/1988 |
| EP | 0 943 306 B1 | 9/1999 |
| EP | 1 243 900 A2 | 9/2002 |
| FR | 1 292 174 A | 4/1962 |
| GB | 1 061 383 | 3/1967 |
| WO | WO 00/09061 | 2/2000 |

\* cited by examiner

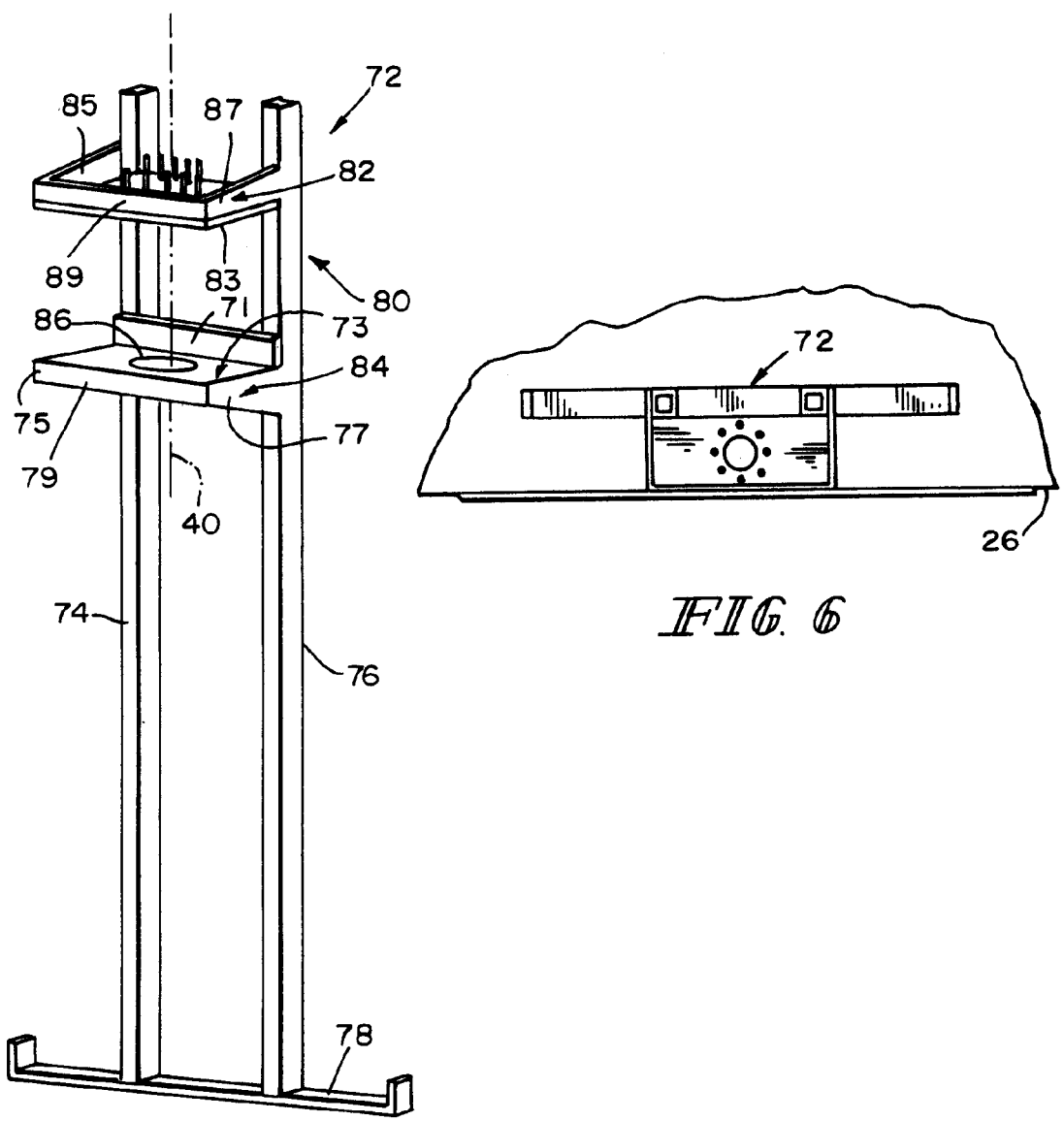
*FIG. 5*
*FIG. 6*
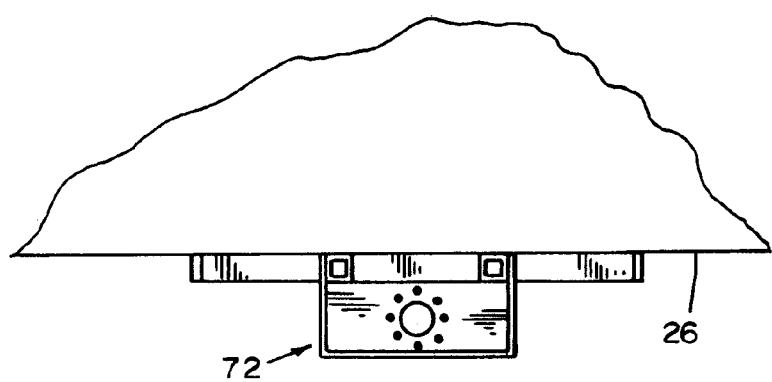
*FIG. 7*

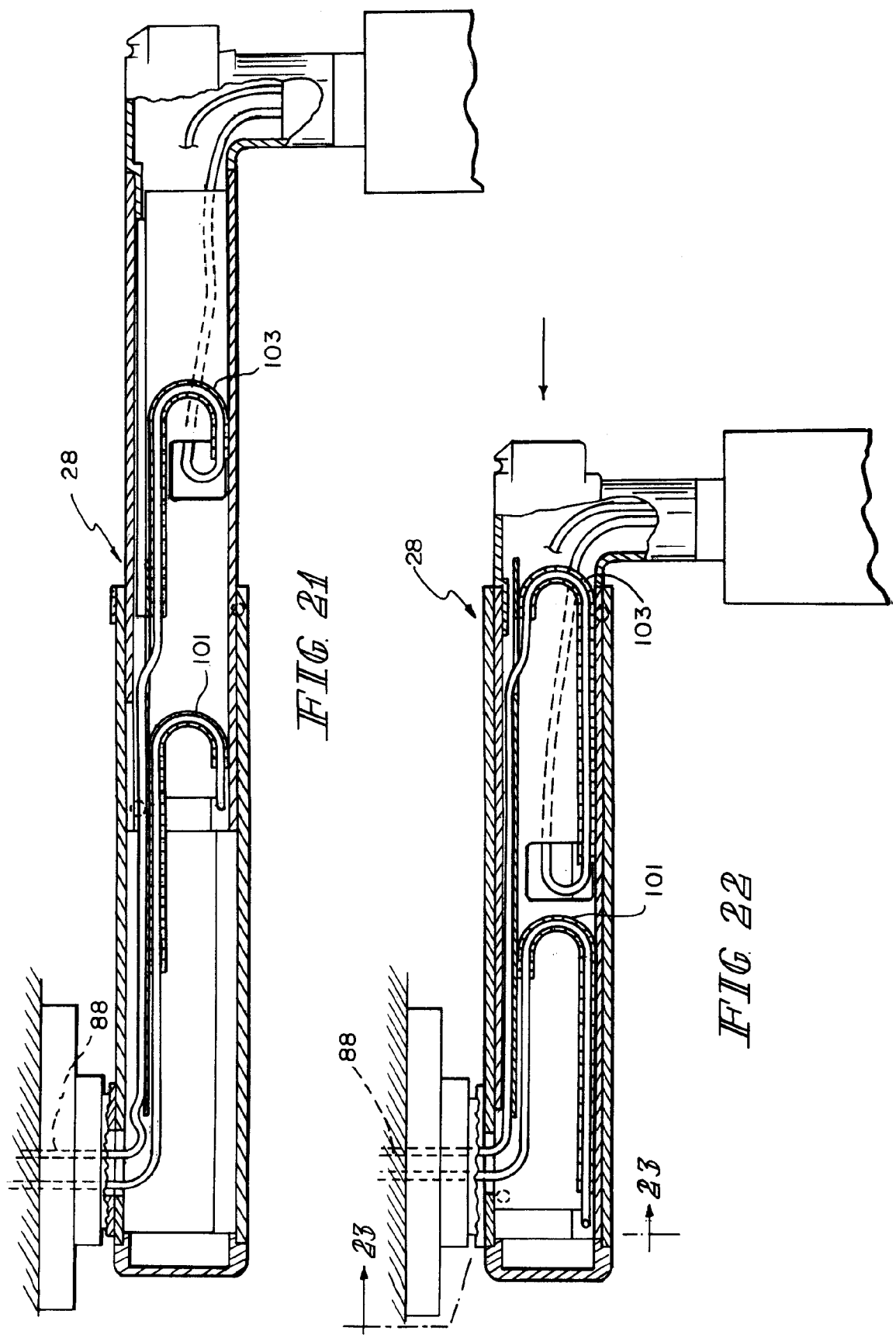

RADIAL ARM SYSTEM FOR PATIENT CARE EQUIPMENT

CROSS REFERENCE TO RELATED APPLICATIONS

This application is a continuation of U.S. patent application Ser. No. 10/802,287 which was filed Mar. 17, 2004, now U.S. Pat. No. 7,065,811, and which is hereby expressly incorporated by reference herein. U.S. patent application Ser. No. 10/802,287 claimed priority under 35 U.S.C. 119(e) to U.S. Provisional Application Ser. No. 60/455,621, filed Mar. 18, 2003 and U.S. Provisional Application Ser. No. 60/510,756, filed Oct. 13, 2003, which are hereby expressly incorporated by reference herein.

BACKGROUND OF THE INVENTION

The present disclosure relates to a system for supporting and housing patient care equipment adjacent a patient support such as a hospital bed, stretcher, chair or the like.

Hospitalized patients often require patient care equipment to be in close proximity during care. Such patient care equipment may include heart monitoring equipment, medical gas delivery equipment, infusion pumps, intra-venous bags, equipment monitors, defibrillators, and other patient care equipment, many of which directly connect to the patient via lines or tubes.

SUMMARY OF THE INVENTION

The present invention comprises one or more of the following features or elements in the appended claims or combinations thereof. A support structure is provided typically to be at the head end of a patient support. The support structure may be configured to be mounted to extend between a hospital floor and ceiling, or upwardly from a hospital floor or downwardly from a hospital ceiling, or it may be configured to extend outwardly from a hospital wall or be embedded in the wall. The support structure may be positioned adjacent a hospital wall. Typically, the structure will be vertically disposed and provide one or more vertical axes about which equipment moves. An arm extends from the support structure and is pivotably movable relative to the structure, typically in a horizontal plane. The arm may be telescoping or fixed in length and comprise a first portion having a mount end pivotably mounted to the support structure and a distal end opposite the mount end. The first portion is pivotable about a pivot axis, and a second portion extends from the distal end of the first portion for telescopic movement relative to the first portion.

A patient care equipment column can be supported by the second portion, the column providing either mounting capabilities for patient care equipment or a service head for patient care equipment, or both. Patient care equipment may be mounted or coupled to an equipment support, and/or patient care equipment may be coupled to any one or more of the services provided by one or more service heads. The column will typically be pivotable about a vertical axis passing through the distal end of the arm.

The support structure may be integrated with or part of a headwall and/or a bed locator. The support structure and/or arm and/or service head and/or headwall may have service outlets, such as for delivery of medical gases or suction, delivery of electrical power, and transmission of data.

Additional telescoping or fixed-length arms may be provided, and may be mounted to the support structure for horizontal pivotable movement about the same pivot axis, or about different axes. Such additional arms may carry a service head, a monitor, and/or patient monitoring equipment.

In some illustrative embodiments, a console or headwall unit is provided, the console providing cabinets or cavities or spaces for housing any one of the service head, the monitor, and the equipment support when these are in respective storage positions.

Additional features will become apparent to those skilled in the art upon consideration of the following detailed description of illustrative embodiments exemplifying the best mode of carrying out various systems for transporting and supporting patient care equipment as presently perceived.

BRIEF DESCRIPTION OF THE DRAWINGS

The detailed description particularly refers to the accompanying figures, in which:

FIG. 5 is a perspective view of the support structure used to support the telescoping and pivoting arms;

FIG. 6 is a top view of the support structure of FIG. 5 built into a wall;

FIG. 7 is a top view of the support structure of FIG. 5 mounted adjacent to a hospital wall;

FIG. 21 is a cross-sectional view of a support arm showing a telescoping arm in an extended position, the arm housing a plurality of line-guides;

FIG. 22 is a cross-sectional view similar to that of FIG. 21, showing the telescoping arm in the retracted position;

DETAILED DESCRIPTION OF THE DRAWINGS

Figures 1, 2:
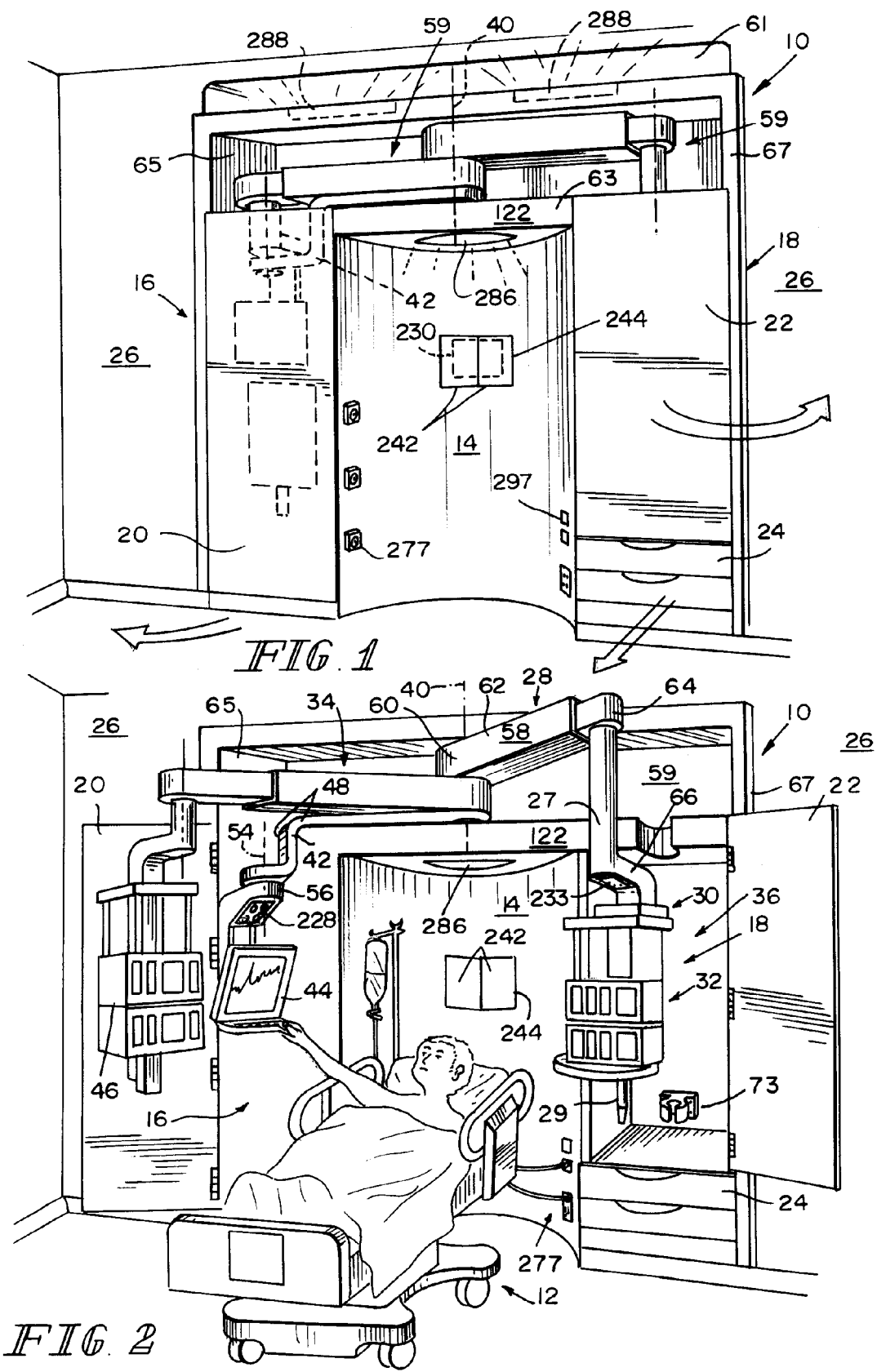
FIG. 1 is a perspective view of a patient care equipment support system built into a headwall.
FIG. 2 is a perspective view of the support system of FIG. 1 having a patient support positioned adjacent thereto, showing cabinets on both sides of the support system opened to expose a set of patient care columns supporting patient care equipment thereon.

A patient care equipment support system 10 is shown in FIG. 1 and a patient support 12 is positioned in front of the system in FIG. 2. Patient support 12 is illustratively a hospital bed positioned in a hospital room, however, it should be understood that the embodiments disclosed herein may be modified to be used with other patient supports, such as operating room tables, stretchers, or any other equipment on which a patient may rest, and in various types of settings including intensive care rooms, operating rooms, and physician offices.

In the embodiment illustrated in FIG. 1, support system 10 comprises a console including a headwall 14 having cabinets 16, 18 positioned on opposite sides thereof. Cabinets 16, 18 illustratively have access doors 20, 22, however, it is within the scope of the invention to utilize other types of doors such as bi-fold doors, pocket doors, or even to leave cabinets 16, 18 without doors. It is within the scope of the disclosure to offer only one cabinet 16 or 18, or to offer no cabinets. An upper space 59 defined by walls 65, 67 may or may not be offered.

Figures 8, 9:
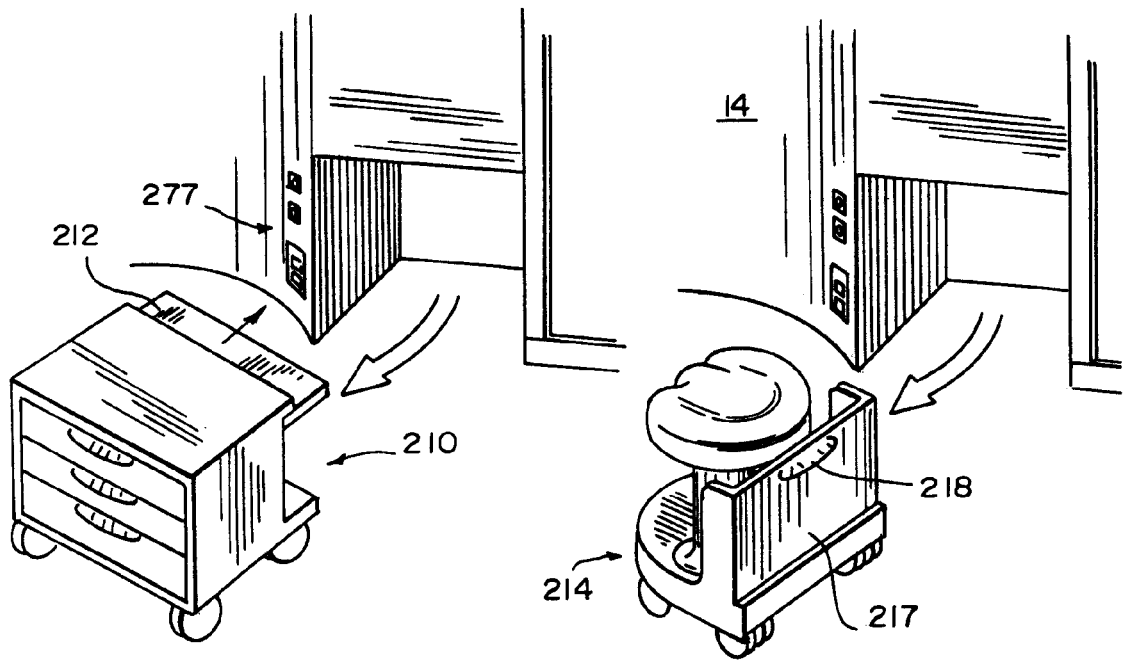
FIG. 8 is a perspective view of a movable cart having drawers and an extendable shelf, the cart storable in a cabinet recess.
FIG. 9 is a perspective view of a stool that can stored in the cabinet recess.
Figure 10:
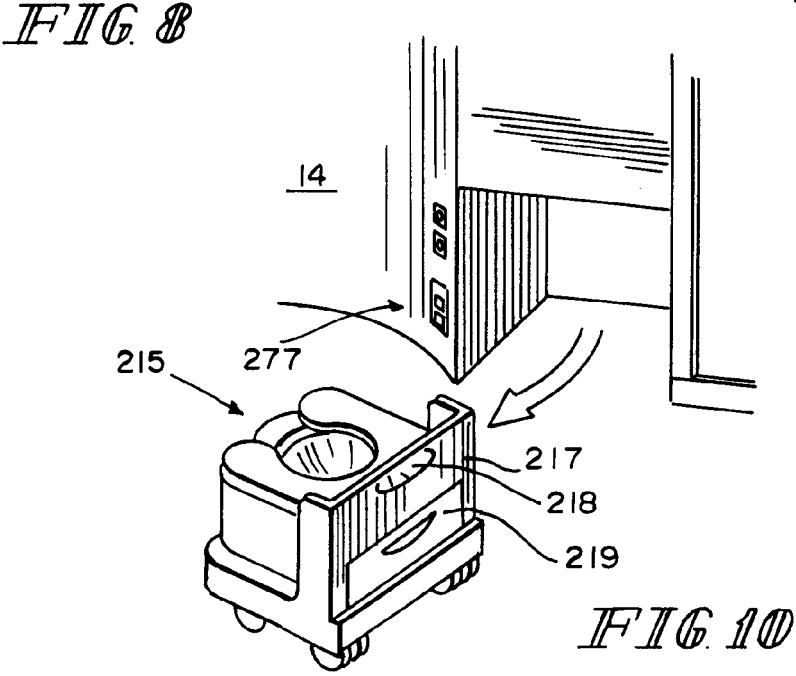
FIG. 10 is a perspective view of a portable toilet that can be stored in the cabinet recess.

FIGS. 1 and 2 show drawers 24 illustratively positioned under cabinet 18 for providing additional storage. However, it is within the scope of the disclosure to replace at least one of drawers 24 with a movable storage cabinet or supply cart 210, such as a cart having an extendable or pivotable (not shown) table 212 attached thereto as shown in FIG. 8. It is also within the scope of the disclosure to provide a pull-out stool 214 for use by a caregiver in the place of drawers 24, as can be seen in FIG. 9. The seat on stool 214 can be movable between a raised use position and a lowered storage position. Stool 214 can be stored in a recess sized to receive the Furthermore, a portable toilet 215 may be provided, as shown in FIG. 28, to be stored in a similarly sized space in the cabinet. Illustratively, each of the stool 214 and portable toilet 215 have an aesthetic facade 217 having a handle 218 to facilitate positioning of the stool 214 or toilet 215. Further illustratively, toilet 215 may have a drawer 219 in which toilet sewage may be stored and accessed, or in the alternative, for other storage.

In the illustrative embodiment shown in FIG. 1, headwall 14 is shaped in a concave fashion such that the central portion of headwall 14 is recessed relative to the edges which contact cabinets 16, 18. Such a configuration permits the head end of patient support 12 to be positioned closer to wall 26 and provides more clearance at the foot end of patient support 12. A bed locator (not shown) can be mounted to headwall 14 for assisting in positioning the bed in a fixed position. It is within the scope of the disclosure to provide headboards, headwalls with other configurations, or to omit the headwall altogether.

Support system 10 is shown in FIGS. 1, 2 and 6 to be substantially flush with wall 26 such that cabinets 16, 18 and other portions of support system 10 are built into wall 26. However, it is should be understood that frame 72 of support system 10 could be positioned such that support system 10 extends outwardly from wall 26, or even be positioned away from wall 26 as an independent structure such as shown, for example, in FIG. 3. In the embodiment illustrated in FIG. 3, a support system 216 is configured to support arms extending from more than one side of the support system. Such a configuration allows for a plurality of patient supports 12 to be positioned near support system 216, support system 216 providing patient care equipment support for the plurality of patient supports 12 simultaneously. Bed locators 25 can be mounted on sides of support column 23.

As can be seen in FIG. 2, doors 20, 22 can be opened to expose the inside of cabinets 16, 18, respectively. A first arm 28 illustratively telescopes horizontally and has a patient care column 27 coupled thereto.

Figure 24:
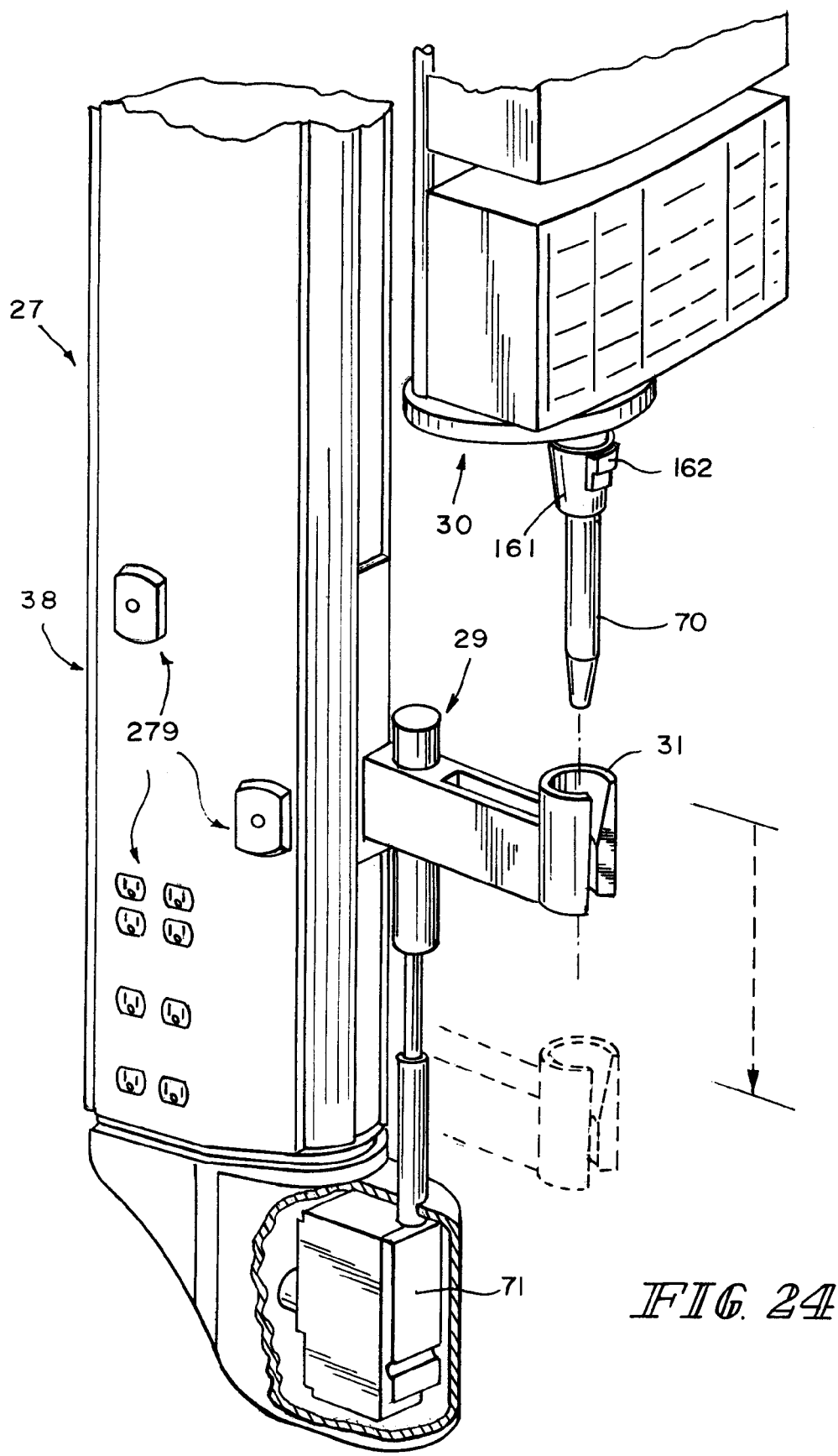
FIG. 24 is a perspective view of a vertically movable equipment support, the equipment support being configured to be mounted on a receiver coupled to a column.

As can be seen in FIG. 24, the patient care column illustratively comprises a first column 27, a second column 29 movable relative to the first column 27, and a post receiver 31 coupled to the second column 29. Post receiver 31 is configured to receive an equipment support 30 having a mount post 70. The illustrative mount post 70 has a tapered collar 161 mounted on an upward portion of the mount post, the collar 161 having a protrusion 162 extending therefrom. Post receiver 31 comprises a substantially C-shaped cross-section that permits the passage of mount post 70 therethrough, while engaging protrusion 162 on mount post 70. Such engagement provides an axial lock that prevents axial movement of mount post 70 when it is docked on post receiver 31.

Illustratively, second column 29 telescopes vertically relative to first column 27 under the power of an electric motor 71, illustratively a Linak LA 31 Linear Actuator with a CB9 central box, housed in first column 27, the electric motor being actuated by either a toggle switch (not shown) positioned on first column 27, or a wired or wireless remote control. Such vertical telescoping movement permits the equipment support 30 to be raised and lowered for optimal placement by a caregiver and for loading of equipment or IV bags by a caregiver. Additionally, such vertical telescoping movement can permit the docking of equipment support 30 on a post receiver mounted on a patient support, as disclosed in the patent application entitled Patient Care Equipment Management System, filed simultaneously herewith having U.S. patent application Ser. No. 10/802,289, such application also being based upon U.S. Provisional Application Ser. No. 60/455,621, filed Mar. 18, 2003 and U.S. Provisional Application Ser. No. 60/510,756, filed Oct. 13, 2003. Other locations for a post receiver 73 are within the scope of the disclosure. For example, a post receiver 73 may be located in a cabinet 16 or 18, thereby permitting the docking of equipment support 30 in a cabinet as can be seen in FIG. 2. In the alternative, a post receiver may be formed in a stand positioned near patient support 12. Illustratively, second column 29 may move as much as 12-18 inches relative to first column 27. It should be understood that drivers such as hydraulic cylinders, magnetic cylinders, pneumatic cylinders, and the like may be used to move column 29 relative to column 27 in lieu of an electric motor.

Figure 19:
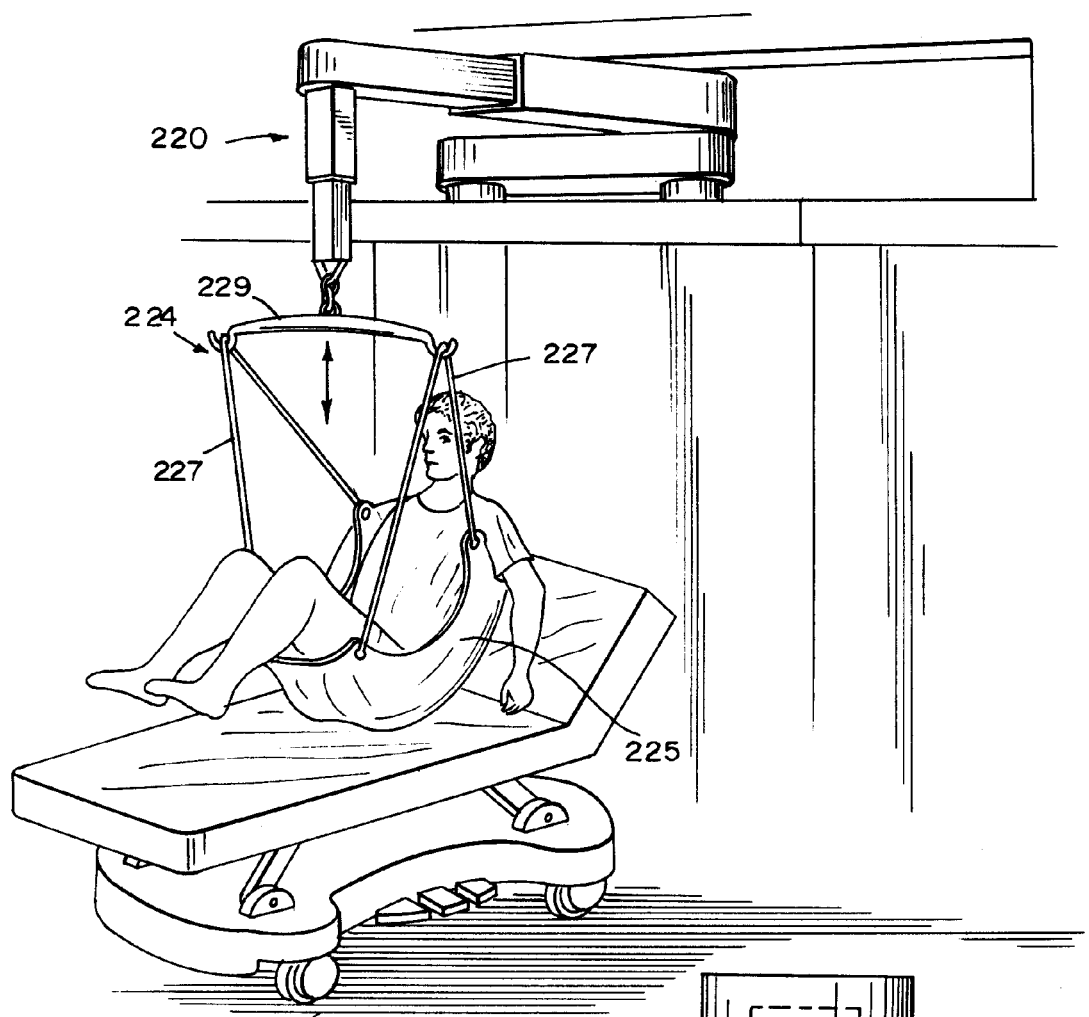
FIG. 19 is a perspective view of a wall-mounted arm supporting a patient lift.
Figure 20:
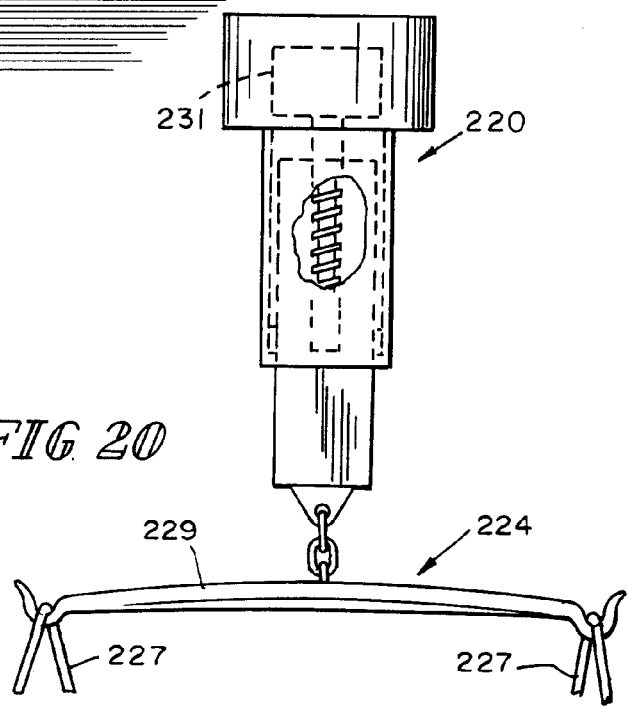
FIG. 20 is a front view of the lift mechanism associated with the use of the patient lift.

In the embodiment shown in FIGS. 19 and 20, column 220 may be configured to support a patient transfer device 224. Patient transfer device 224 illustratively comprise a body sling 225 supported by tethers 227 on a hangar 229, but other patient transfer devices are within the scope of the disclosure. For example, an assist handle, a mattress support, or other variations of devices designed to lift, transfer and/or move patients are contemplated.

Illustratively, column 220 may vertically extend or retract as much as 12-18 inches relative to first arm 28. Such vertical movement may be achieved by an electric motor, hydraulic cylinder, magnetic cylinder, pneumatic cylinder, or the like. Illustratively, the vertical movement is achieved with an electric motor 231 having a screw drive.

Equipment support 30 is configured to support patient care equipment thereon, as can be seen in FIG. 2. Equipment support 30 illustratively includes a secondary service head 233 that can provide requisite electricity and services to an infusion management system 32, as pictured in FIG. 2. Illustratively, equipment support 30 is configured to hold IV bags on an upper portion 36 of support frame 30, and infusion management systems 32 can be mounted on a lower portion of equipment support 30.

While patient support columns are illustrated and described herein as either equipment supports, service heads, structures for carrying equipment supports, structures for carrying patients, or a combination thereof, it should be understood that patient support columns may comprise any other device or element that could be connected to an arm in a hospital room, operating room, or doctor's office. As used herein, the word "column" generally refers to a vertically disposed structure mounted on an arm, and the word "arm" generally refers to a horizontally disposed structure. However, these definitions should not be construed as limiting to the possibility of other embodiments in which columns are other than generally vertical and/or in which arms are other than generally horizontal.

Figure 3:
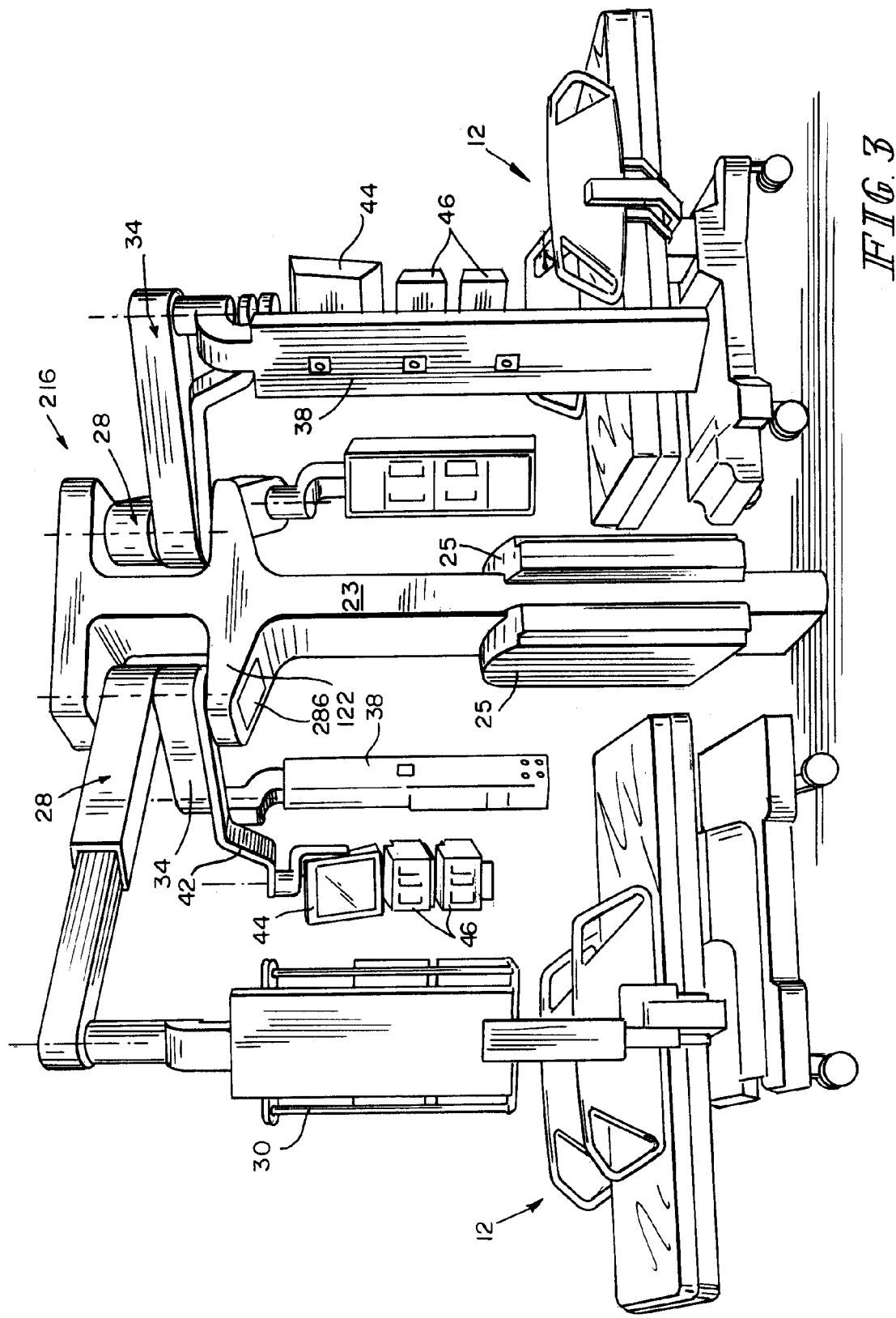
FIG. 3 is an embodiment of a support system showing a plurality of arms moved to a variety of positions to support associated patient care equipment and service heads in desired locations relative to a pair of patient supports.

A second arm 34 is illustratively provided in FIGS. 2 and 3, and is illustratively telescoping in length and can also carry a column supporting patient care equipment. Either or both columns may also comprise a main service head 38, visible in FIG. 24, which may provide medical air, oxygen, medical vacuum, nitrogen, nitrous oxide, electronic data connectivity, and electricity, among other services that may be needed specific to the use of support system 10. Illustratively, such services have been positioned at sufficiently raised locations so as to allow a caregiver to access the service ports 279, while the dragging of medical lines and tubes is prevented. Such services could be arranged so that there is a "dry" column and a "wet" column. A dry column, for example, may include electronic monitoring equipment, communication ports, medical air, oxygen, medical vacuum, nitrogen, nitrous oxide ports, and a ventilator. A wet column may include IV fluids, pumps, and medications.

In some embodiments a column may support other hardware, including patient monitor 44, satellite modules 46, an examination or other light, or other items.

As can be seen in FIGS. 1 and 2, second arm 34 may be pivoted coaxially about the same pivot axis 40 as that which first arm 28 pivots about. However, it is within the scope of the disclosure to utilize separate pivot axes. For example, first and second arms 28, 34 may be spaced apart on a wall such that first and second arms 28, 34 have parallel pivot axes, or first and second arms 28, 34 may be positioned on separate walls, as can be seen in FIG. 4

Figure 4:
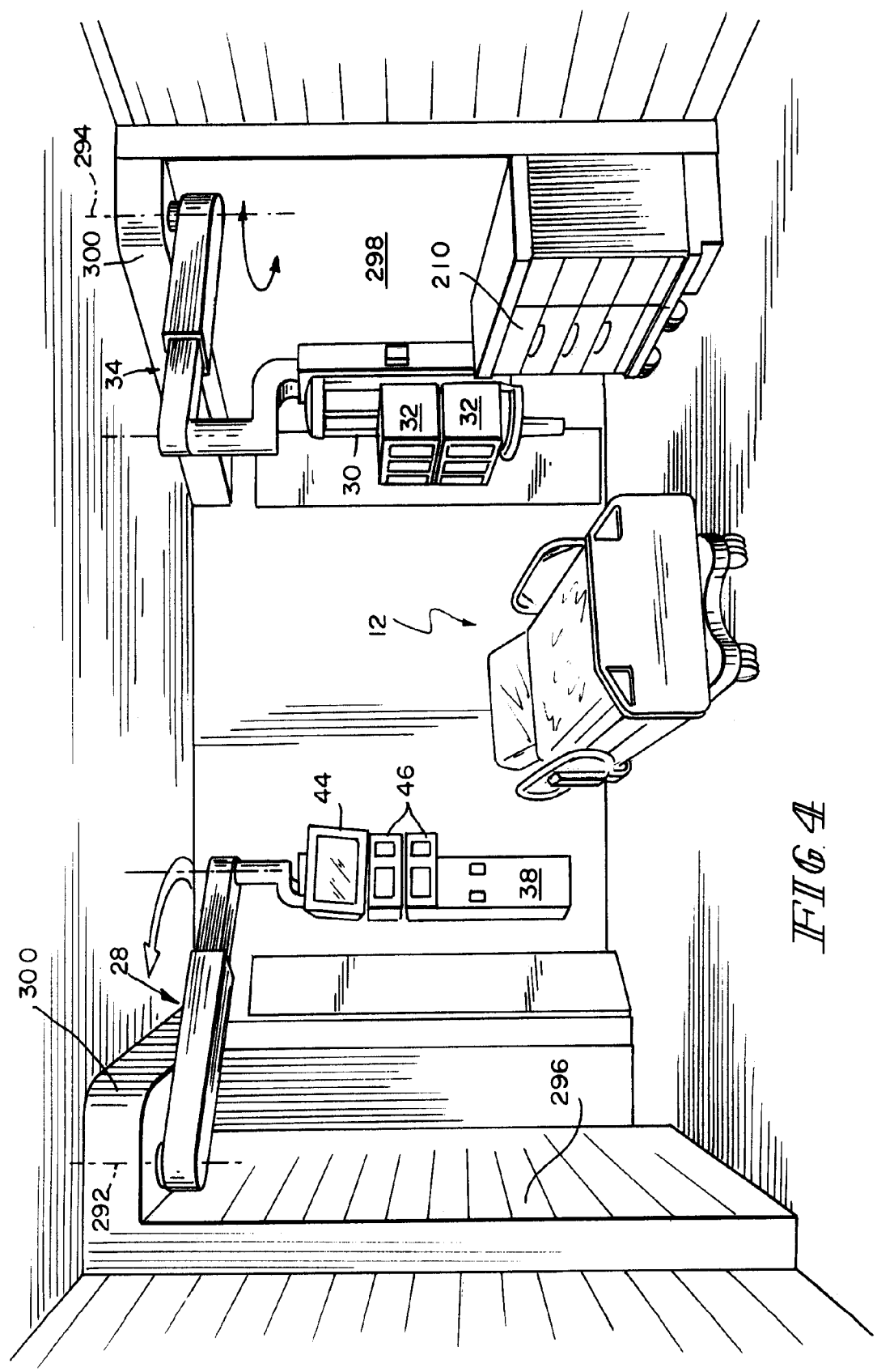
FIG. 4 is another embodiment of a support system showing arms extending from support structures adjacent opposite walls toward a patient support.

In the embodiment shown in FIG. 4 first arm 28 pivots about an axis 292 proximal to wall 296 and second arm 34 pivots about an axis 294 proximal to wall 298. Axes 292, 294 are illustratively parallel. Arms 28, 34 are shown supported by an upper platform 300 and can be further supported by a lower platform. A supply cart 210 is illustratively provided in the room.

The illustrative infusion management systems 32 are manufactured by Alaris and are sold under the name Medley Medication Safety System. However, it should be understood that the disclosed equipment support 30 is configured for use with the products of any number of infusion management system manufacturers. It is also within the scope of the disclosure to mount infusion management systems 32 to main service head 38, or on any other column or arm provided by support system 10.

A third arm 42 is provided in the illustrative system 10, shown in FIGS. 1 and 2. Third arm 42 is illustratively fixed in length and carries a patient monitor 44, and can also carry a computer or satellite modules. Such satellite modules may incorporate various monitoring devices for monitoring a patient's condition. Patient monitor 44 displays information relating to the patient's condition.

Illustratively, third arm 42 may carry patient monitor 44, while another column carries satellite modules 46. Satellite modules 46 may be manufactured by Hewlett-Packard and marketed under the name Veridia System, but other modules or devices for monitoring a patient's condition can conceivably be carried by third arm 42. Third arm 42 may have a service head portion 228, as can be seen in FIG. 2. Such a service head portion illustratively provides electricity and data ports, but other services may be provided and are within the scope of the disclosure.

Service ports 277 may also be provided in headwall 14, as can be seen in FIGS. 1 and 2. In such an embodiment, selected services 279 may still be provided on a column. Illustratively, two telescoping arms are provided, but it is within the scope of the disclosure to utilize one or more arms fixed in length.

Patient monitor 44 may be embodied to be used by the patient in addition to a caregiver, or patient monitor 44 may be configured for use by only the patient. In such embodiments, as shown in FIG. 2, the patient can view television programming, educational programming, or other information offered by the hospital or physician's office.

A computer 230, shown in FIG. 1 (in phantom), may be carried by an arm or may be mounted inside the console or any other location conveniently accessed. Computer 230 is illustratively mounted inside a space 244 in headwall 14 that is enclosed by doors 242 in FIGS. 1 and 2.

Illustratively, third arm 42 is constructed of two tubular beams 48 which extend outwardly in spaced apart relation, the two tubular beams 48 angling downwardly in a distal region thereof to join together at their distal ends, forming a central support for equipment support 56. Third arm 42 illustratively pivots about pivot axis 40 in a fashion similar to that of first arm 28 and second arm 34, although it is within the scope of the disclosure to have third arm 42 pivot about a separate axis.

In the illustrated embodiment, equipment that is carried by each of first arm 28, second arm 34, and third arm 42 is pivotable about a second distal axis that is parallel to pivot axis 40. For example, patient monitor 44 is positioned on an equipment support 56 that is pivotable about pivot axis 54 relative to third arm 42. Such dual pivoting movement permits the equipment on each of the arms to be accessible from a wide range of locations. Each arm may further be telescoping, which provides even greater flexibility and movement of the arms and attached columns.

First arm 28 is illustratively telescoping and comprises a first portion 58 that has a mount end 60 mounted for pivotable movement about pivot axis 40 and a distal end 62 extended away from mount end 60 as shown in FIG. 2. First arm 28 further comprises a second portion 64 that is coupled to the distal end of the first portion and configured to telescope relative to first portion 58. Such telescoping movement allows equipment support 30 to extend beyond the radial lengths of second and third arms 34, 42, providing the option of positioning first arm 28 on either side of arms 34, 42, thereby giving a caregiver additional flexibility in setting up patient care equipment about a patient. Additionally, such telescoping movement allows a service head or any other column to be positioned in a greater range of locations relative to the patient support 12.

In a similar fashion, second and third arms 34, 42 can also pass by each other to switch places. If only one arm is telescoping, it could be positioned vertically above or below the other arms, facilitating movement of the arms past each other.

As can be seen in FIGS. 1 and 2, an upper space 59 can be provided that illustratively extends horizontally for substantially the length of the console. Upper space 59 is illustratively of sufficient depth to allow arms 28, 34, 42 to be positioned in their storage positions inside upper space 59. Upper space 59 is bounded on the upper side by wall 61 (which houses upper platform 82), and on the lower side by wall 63 (which houses lower platform 84). Upper space 59 is also bounded by side wall 65, extending vertically along one side of the console to simultaneously form a side wall for cabinet 16, and side wall 67, extending vertically along the other side of the console to form a side wall for cabinet 18.

Cabinets 16, 18 illustratively have interior regions or spaces that communicate with upper space 59 so that when arms 28, 34, 42 are in their storage positions, as shown in FIG. 2, columns 30, 38, 56 depend from the arms into the associated spaces of storage cabinets 16, 18. Illustratively, the console is configured such that arms 28, 34, 42 and columns 30, 38, 56 can be stored completely within the console, without elements protruding from the console.

It should be understood that various embodiments and configurations for the console are within the scope of the disclosure. Such a console may be sold to include only one cabinet 16 or 18. The console may be sold without an upper space 59 bounded by walls, or it may be sold with only a headwall 14.

Lighting, whether ambient or for reading or examination purposes, may illustratively be mounted on the console, on an arm, and/or on a column. A console light 286 may be built in to lower pier 122, as can be seen in phantom in FIG. 1 and in FIG. 3. Ambient lights 288 may be mounted above the console to provide ambient lighting for the room, as can be seen in FIG. 1.

It should be understood that third arm 42 and equipment support 56 (illustratively carrying patient monitor 44) can be moved adjacent to either column. A recess 66 is illustratively formed in the upper portion of each column. Such recess 66 being configured to receive equipment support 56 when third arm 42 is aligned parallel to the selected first or second arm.

Figure 23:
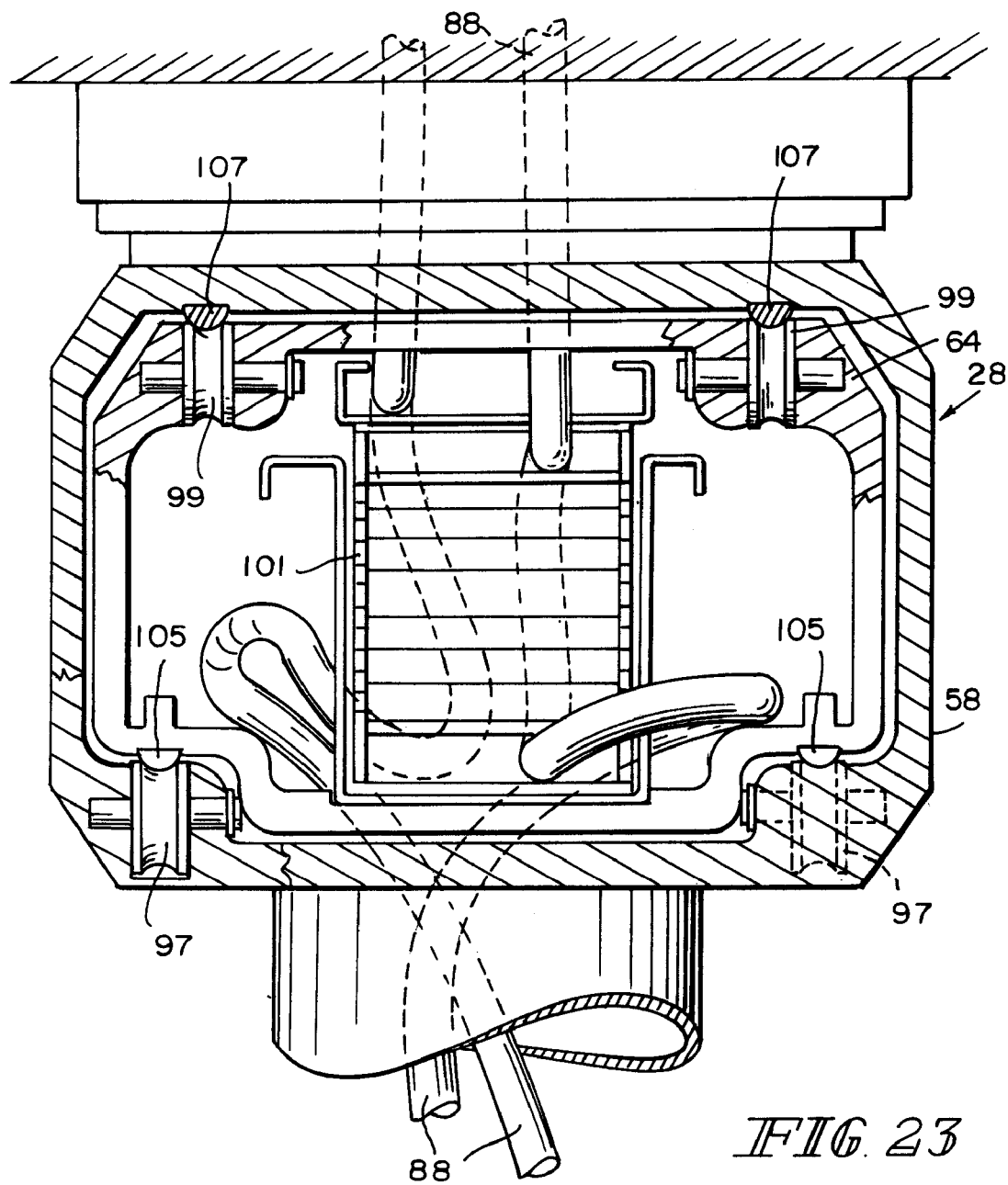
FIG. 23 is a cross-sectional view taken along the line 23-23 of FIG. 22, showing placement of the lines inside the telescoping arm and the line-guides.

As can be seen in FIG. 5, the illustrative support system 10 includes a support structure frame 72 that is configured to extend between a hospital floor and a ceiling, which could be supported with a ceiling truss or ceiling support system. Such a ceiling truss or ceiling support system may need to be reinforced with support bars. The support structure frame 72 illustratively comprises a first vertically extending member 74 and a second vertically extending member 76. A horizontal stabilizer 78 is mounted to the bottom of both vertically extending members 74, 76. An arm mount portion 80 extends laterally and between vertically extending members 74, 76. The arm mount portion comprises an upper platform 82 and a lower platform 84. Upper and lower platforms 82, 84 each have a hole 86 defined therein. A shaft or collar structure for arms 28, 34, 42 is mounted between the holes such that arms 28, 34, 42 can each individually pivot about pivot axis 40. As can be seen in FIGS. 21 and 23, conduits or service lines 88 are illustratively dropped from the ceiling and selectively routed through arms 28, 34, 42 to provide medical air, oxygen, vacuum, nitrogen, nitrous oxide, telephone/data connectivity, and/or electricity, among other services that may be needed specific to the use of support system 10.

As can be seen in FIG. 5, lower platform 84 comprises a back wall 71 coupled to a front side of vertically extending members 74, 76 to define a vertical plane. Horizontal surface 73 cantilevers outwardly from back wall 71 and is supported by side supports 75, 77 that extend downwardly and also couple to vertically extending members 74, 76. A lip 79 extends downwardly from a front edge of horizontal surface 73, lip 79 being further coupled to front edges of side supports 75, 77.

Similarly, upper platform 82 comprises a back wall coupled to a front side of vertically extending members 74, 76 to define a vertical plane. Horizontal surface 83 cantilevers outwardly from back wall 81 and is supported by side supports 85, 87 that extend upwardly and also couple to vertically extending members 74, 76. A lip 89 extends upwardly from a front edge of horizontal surface 83, lip 89 being further coupled to front edges of side supports 85, 87.

Illustratively, vertically extending members 74, 76 are positioned adjacent wall 26 as shown in FIG. 7. However, it should be understood that vertically extending members 74, 76 may be built into the wall, as shown in FIG. 6, or completely self-standing away from any wall, depending on the placement need for support system 10. Other embodiments of support structures are within the scope of the disclosure, including support structures that extend from the hospital floor but do not touch the ceiling, support structures that extend from the ceiling and do not touch the floor, and support structures that extend from the wall. It is also contemplated that the support structure may extend from either the ceiling or floor and connect to the adjacent wall.

As can be seen in FIG. 3, multiple support structure frames may be placed adjacent each other to provide a support system 216 capable of supporting arms over a plurality of patient supports 12.

Figure 12:
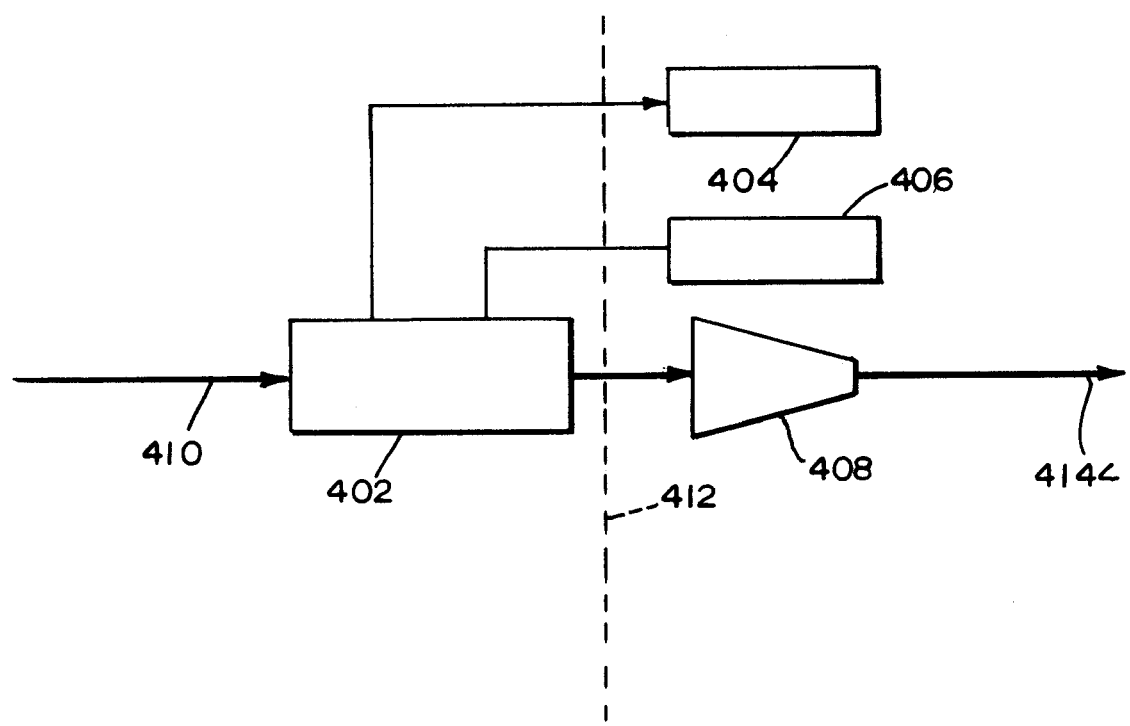
FIG. 12 is a diagrammatic view of a gas port showing nozzles, a display, and controls mounted on the exterior of a caregiver interface, and showing a digital flow meter mounted on the interior.

Columns may include integrated flow meters, which are schematically shown in FIG. 12. A digital flow meter 402 is positioned internally in a column, and display 404, controls 406, and gas nozzle 408 are located such that a caregiver can access or view them from the outside of the column. The internal placement of the digital flowmeter removes one or more items from the cluster of elements normally attached at the gas nozzle area. The gas or fluid is directed to flow into the flow meter 402 as shown by arrow 410, flow through the column interface 412 and out of nozzle 408 in the direction indicated by arrow 414.

Figure 11:
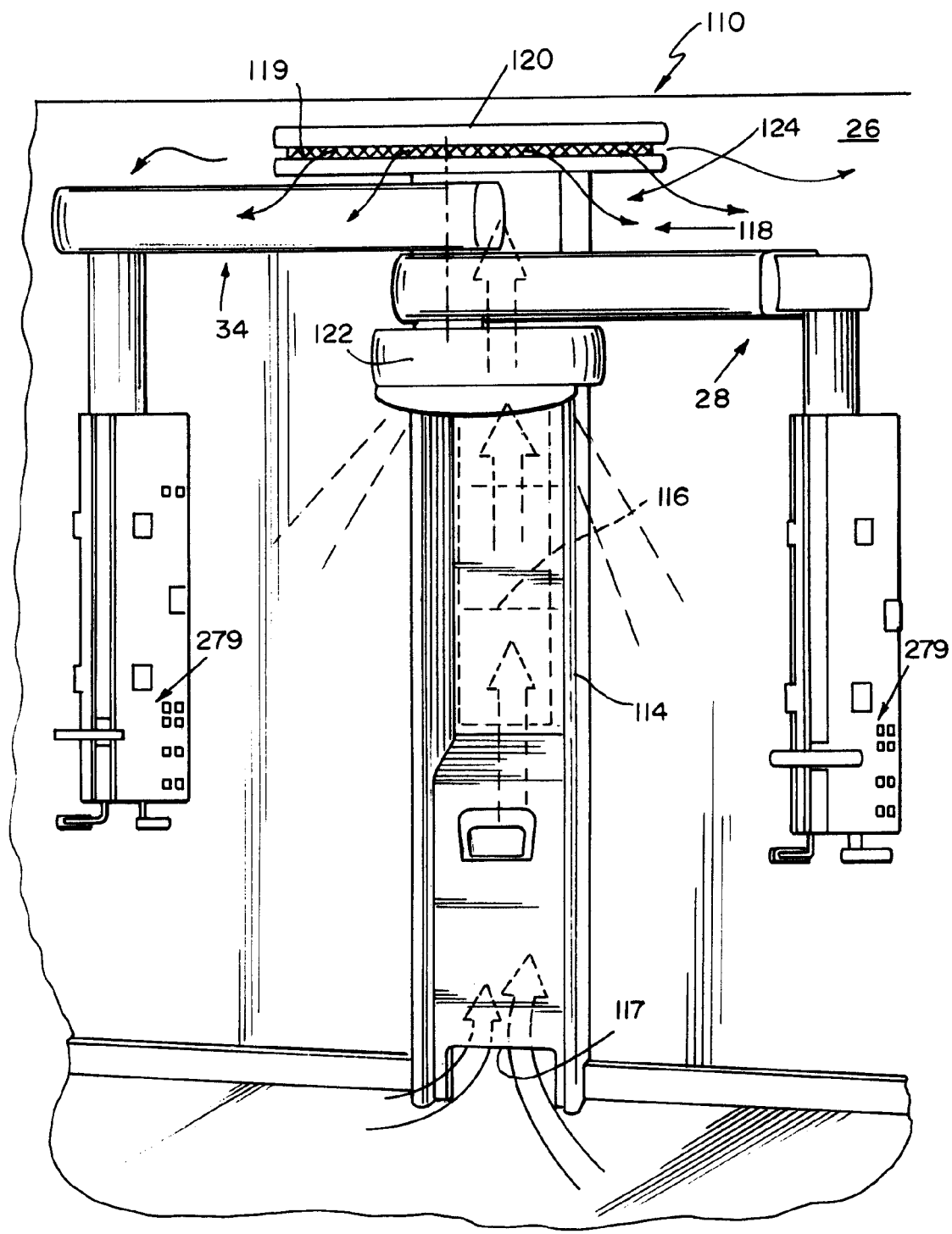
FIG. 11 is a perspective view of a HEPA filtration system built in to a wall-arm support structure.

FIG. 11 shows another embodiment of a patient care equipment support system 110, wherein a headwall 114 with a built-in HEPA (High Efficiency Particulate Air) filtration system 116 is provided, and cabinets and drawers are omitted from the system. Headwall 114 is illustratively configured to have an arm support portion 118. Arm support portion 118 illustratively has an upper pier 120, a lower pier 122, and a channel 124 formed therebetween. Channel 124 is formed so that arms 28, 34 can pivot about their pivot axes to extend through either side of channel 124.

Illustratively, HEPA filtration system 116 comprises an air inlet 117 in a lower portion of headwall 114, and an air outlet 119 that is configured to disperse the air through upper pier 123. The HEPA filtration system 116 is illustratively built into the headwall 114 and can be serviced through an access door (not shown).

Figure 18:
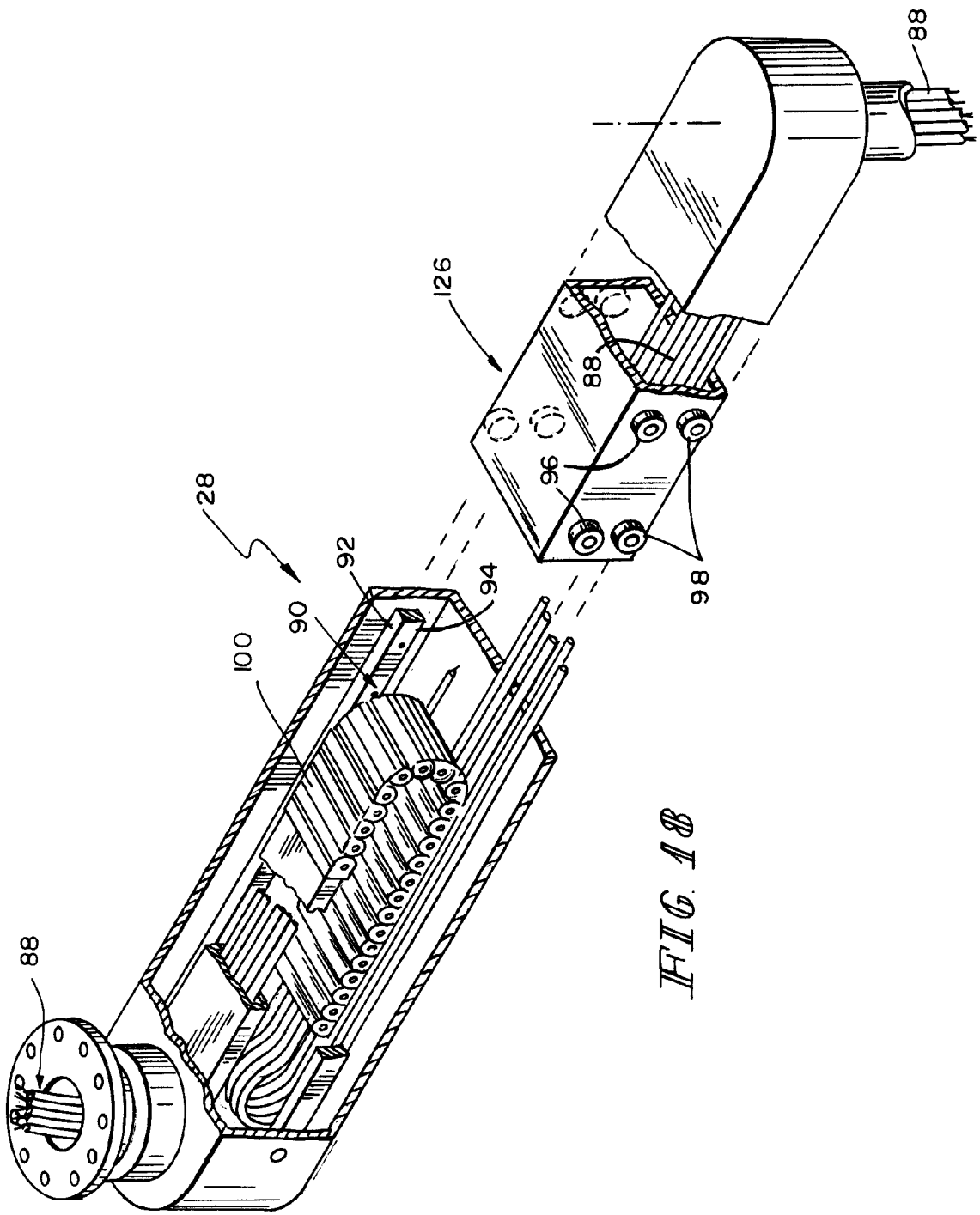
FIG. 18 is a perspective view of a telescoping arm having a line-guide system housed therein.

FIG. 18 shows a cutaway view of a telescoping arm, illustratively first arm 28. A linear bearing assembly 126 supports second portion 64 for horizontal telescoping movement relative to first portion 58. Illustratively, first arm 28 includes a longitudinal bearing member 90 having a flat upper surface 92 and a lower surface 94 defining a V-shaped edge (not shown). Upper bearing wheels 96 engage upper surface 92, and lower bearing wheels 98 define a V-shaped groove for engagement with lower surface 94 of bearing member 90. Other embodiments of bearing assembly 126 are within the scope of the disclosure. For example, the cross-sectional view of arm 28 shown in FIG. 23 illustrates a bearing assembly having lower bearing wheels 97 mounted on the bottom portion of first portion 58 of arm 28, and upper bearing wheels 99 mounted on second portion 64 of arm 28. Tracks 105 are mounted on second arm portion 64 and tracks 107 are mounted on first portion 58.

Service lines 88 are grouped and integrated into an energy chain management system 100 to ensure tangle-free operation of the electrical lines and gas tubing. Illustratively, energy chain management system 100 is a flexible polymer chain link conduit that serves to guide the service lines through the telescoping arm while preventing their entanglement with each other or other objects. The "S"-shape and the flexibility accommodate the telescoping movement of the arm. It should be understood, of course, that any number of energy chains is within the scope of the disclosure. For example, two energy chains 101, 103 are provided in FIGS. 21 and 23 in order to separate electric service lines from others, facilitating future service on the service lines. Energy chain management system 100 is commercially available through Igus Inc. of East Providence, R.I., and is marketed under the trademark E-Chain, however, it should be understood that variations and alternative constructions to energy chain management system 100 are within the scope of the disclosure, as well as other constructions for first arm 28 as a whole.

Figure 13:
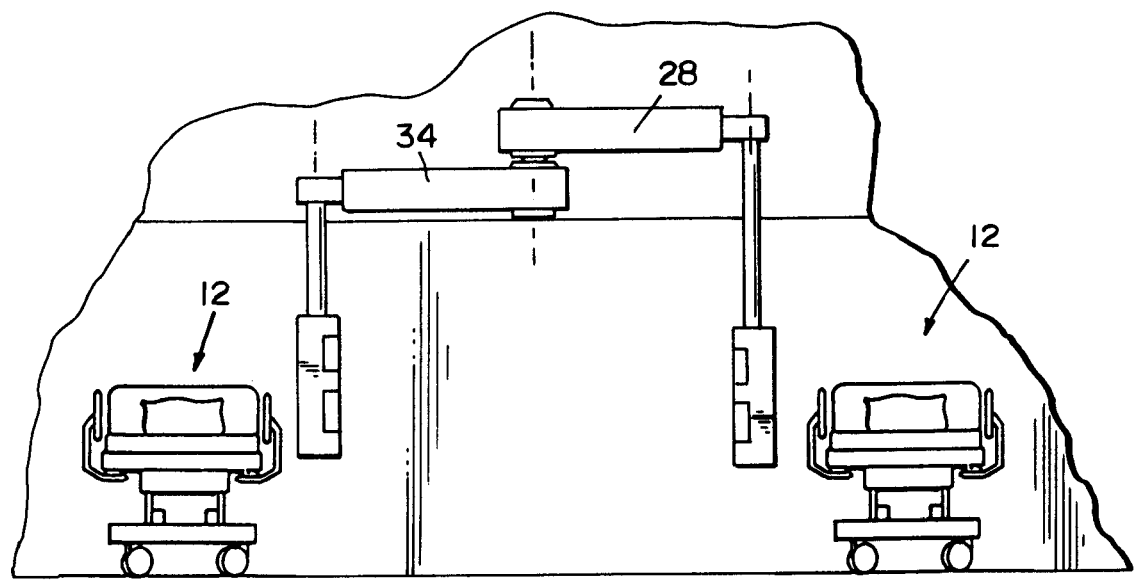
FIG. 13 is a front elevation view of an equipment support system configured to have a plurality of arms supporting columns that can be used with a plurality of patient supports.
Figure 14:
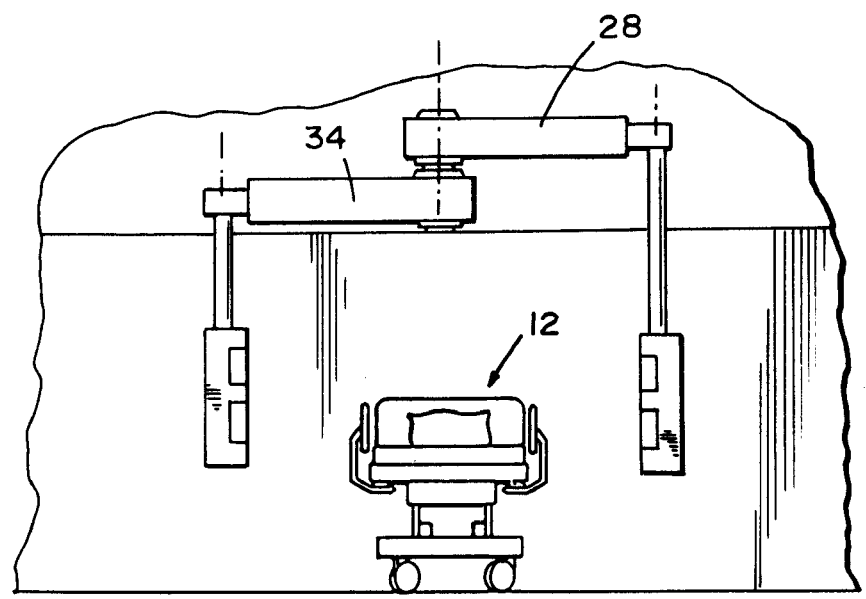
FIG. 14 is a front elevation view similar to that of FIG. 13, showing a plurality of arms supporting columns that can be used with a single patient support.

It should be understood that the presently disclosed system can be modified to provide care in a number of different environments, as shown in FIGS. 13-17. For example, as shown in FIG. 14, a first arm 28 and a second arm 34 can be positioned on opposite sides of a patient support 12. However, the first and second arms 28, 34 can be also divided between two different patient supports 12, as shown in FIG. 13. Such use may be required when a hospital is more crowded and more than one patient is necessarily placed into the patient care environment.

Figure 15:
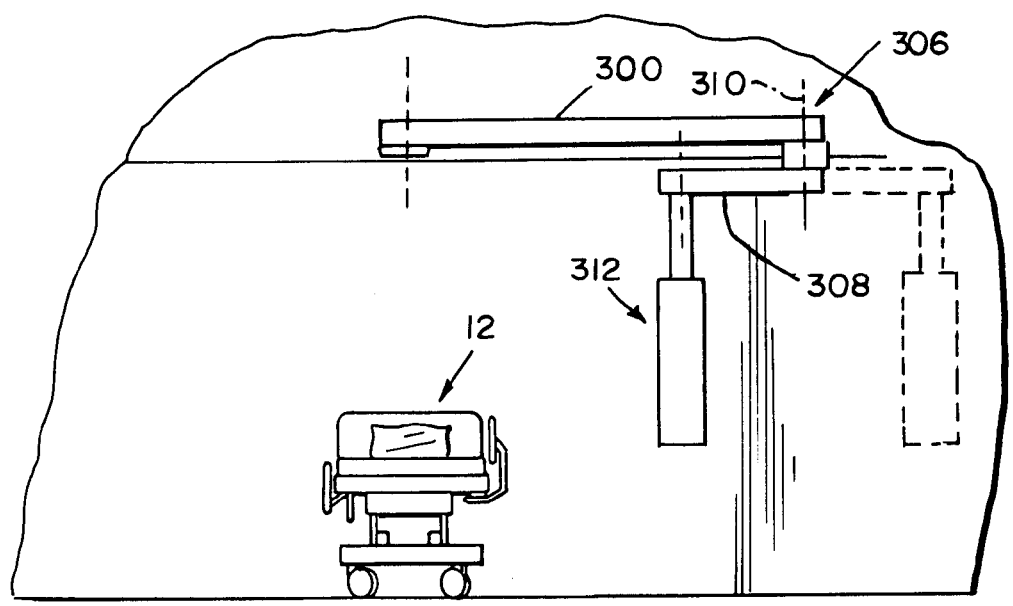
FIG. 15 is a front elevation view of an equipment support system having a wall-mounted pivotable arm with an elbow.
Figure 16:
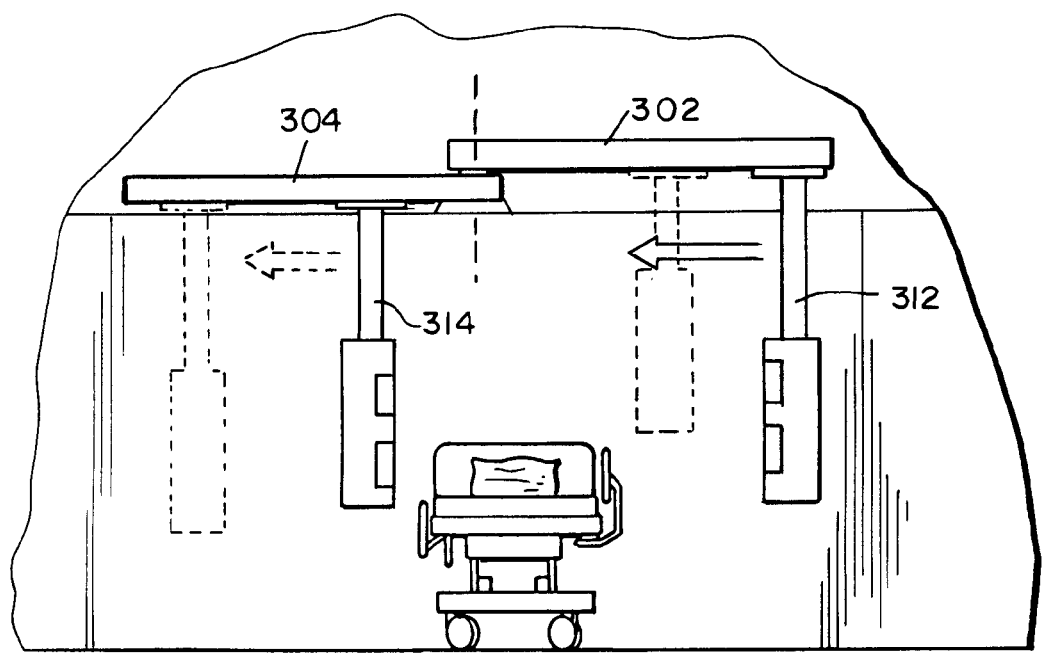
FIG. 16 is a front elevation view of another embodiment of an equipment support system having a wall-mounted pivotable arm that houses a track for movement of the column relative to the track.

FIGS. 15 and 16 show still further embodiments for arms. For example, as shown in FIG. 15, arm 300 may have an elbow 306 that permits pivotable movement of a second arm 308 about pivot axis 310. Such a configuration could be used in place of or in addition to a telescoping arm, thereby providing greater movement of column 312.

Figure 17:
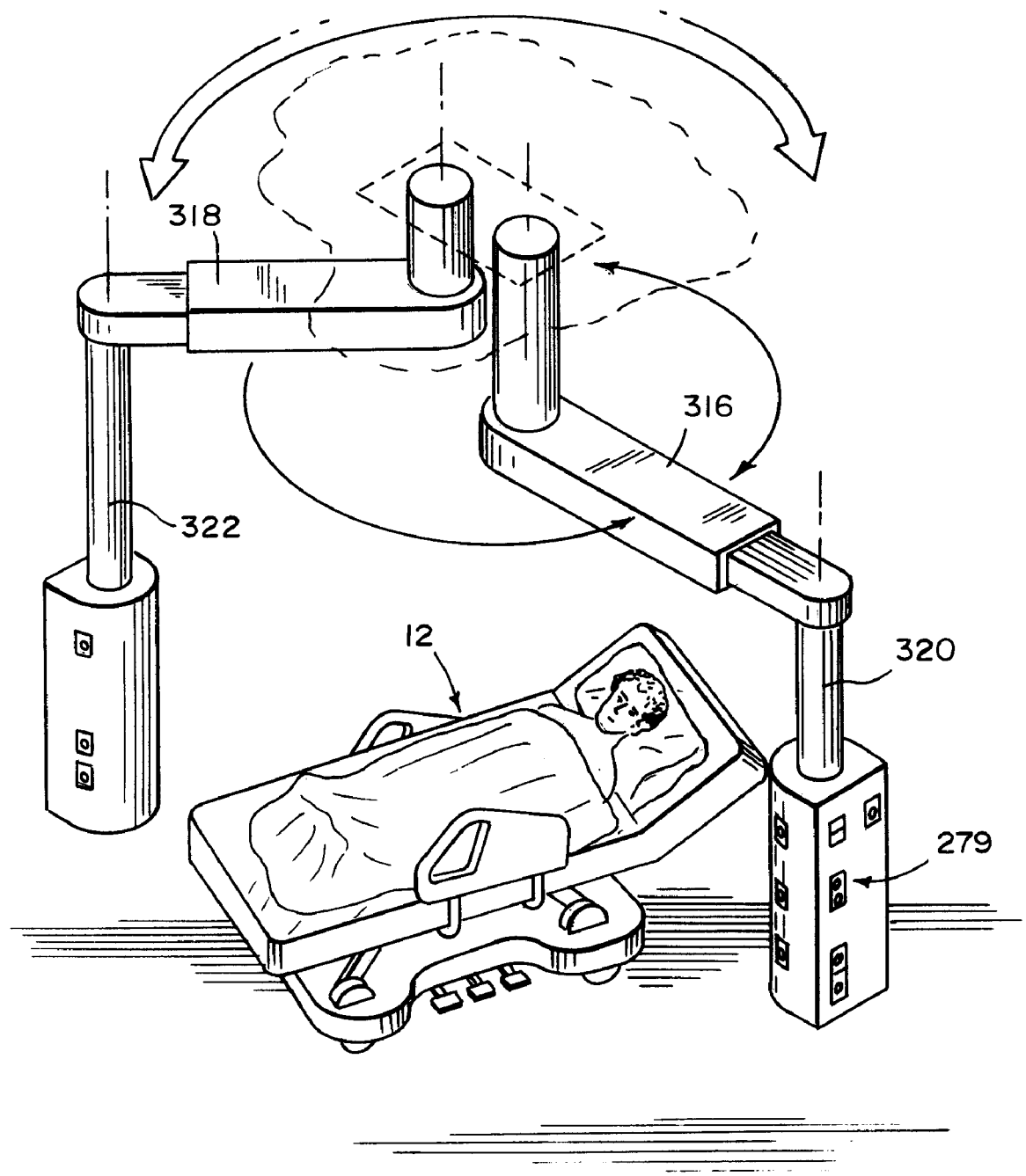
FIG. 17 is a perspective view of yet another equipment support system having a plurality of pivotable, telescoping arms that can be positioned at a large range of places around a patient support.

As shown in FIG. 16, arms 302, 304 may have slidable columns 312, 314 that move along tracks built into arms 302, 304. Furthermore, as shown in FIG. 17, a support structure may be mounted to hang from a ceiling and support telescoping arms 316, 318 that can carry columns 320, 322, such arms 316, 318 being permitted to pass each other as required by telescoping one arm 318 to pass radially outside of arm 316. It should be understood that the use of one or more fixed-length arms instead of telescoping arms is still within the scope of the disclosure.

The illustrated embodiments provide for flexible arrangement of patient care devices, permitting a patient's care to be tailored to various levels of acuity without movement between rooms or support systems 10. Cords and lines running below the patient support can be reduced or eliminated. Unused portions of such patient care devices can be stowed in cabinets 16, 18 or moved out of the way, facilitating care of the patient and movement about the patient. Such a support system 10 can eliminate the need for IV stands near a patient support 12. Furthermore, the support system 10 removes from the patient's direct overhead view the ceiling-mounted arm support structure.

Although the invention has been described in detail with reference to certain illustrative embodiments, variations and modifications exist with the scope and spirit of this disclosure as described and defined in the following claims.

The invention claimed is:

1. A patient care equipment support system for use in a hospital room having a floor and a ceiling, the patient care equipment support system comprising
   a support structure extending from the floor to the ceiling of the room,
   a telescopic arm mounted to the support structure for pivotable movement in a generally horizontal plane,
   a patient care column supported by the telescopic arm,
   an electrical line having portions disposed in the telescopic arm and disposed in the patient care column, and
   a gas conduit having portions disposed in the telescopic arm and disposed in the patient care column.

2. The support system of claim 1, further comprising at least one guide mechanism to guide the movement of the portion of the electrical line disposed in the telescopic arm and the portion of gas conduit disposed in the telescopic arm as the telescopic arm extends and retracts.

3. The support system of claim 2, wherein the at least one guide mechanism comprises a first flexible cater disposed in the telescopic arm to guide the movement of the portion of the electrical line disposed in the telescopic arm and a second flexible cater disposed in the telescopic arm to guide movement of the portion of the gas conduit disposed in the telescopic arm as the telescopic arm extends and retracts.

4. The support system of claim 3, wherein the first and second flexible carriers move in tandem when the telescopic arm extends and retracts.

5. The support system of claim 3, wherein the second flexible carrier is radially spaced apart from the first flexible carrier.

6. The support system of claim 1, wherein the column has an electrical outlet thereon at which the electrical line terminates.

7. The support system of claim 1, wherein the column has a gas outlet thereon at which the gas conduit terminates.

8. The support system of claim 1, wherein the gas conduit supplies at least one service selected from the group comprising: medical air, oxygen, vacuum, nitrogen, and nitrous oxide.

9. The support system of claim 1, wherein the electrical line supplies at least one service selected from the group comprising: electronic data connectivity and electrical power.

10. The support system of claim 1, wherein the patient care column comprises a post receiver configured to receive a post of an equipment support apparatus.

11. The support system of claim 1, wherein the patient care column is pivotable relative to the telescopic arm about a generally vertical axis.

12. The support system of claim 1, wherein the telescopic arm is pivotable in the generally horizontally plane about a generally vertical first axis and the patient care column is pivotable relative to the telescopic arm about a generally vertically second axis that is generally parallel to the first axis.

13. The support system of claim 1, further comprising a console configured to house at least a portion of the support structure.

14. The support system of claim 13, wherein the console comprises a cabinet configured to house the patient care column.

15. The support system of claim 13, wherein the console comprises a contoured panel configured to receive a bead end of a patient support.

16. The support system of claim 15, further comprising a service port mounted on the contoured panel, the service port providing at least one service selected from the group comprising: medical air, oxygen, vacuum, nitrogen, nitrous oxide, electronic data connectivity, and electricity.

17. The support system of claim 1, wherein the support structure comprises at least two generally vertically extending support members and an arm mount portion extending therefrom in a cantilevered manner and wherein the telescopic arm is coupled to the arm mount portion.

18. The support system of claim 1, further comprising a patient monitor coupled to the column.

19. The support system of claim 18, wherein the patient monitor is configured to report a status of the patient to a caregiver.

20. The support system of claim 18, wherein the patient monitor is configured to transmit television programming to the patient.

* * * * *

UNITED STATES PATENT AND TRADEMARK OFFICE
CERTIFICATE OF CORRECTION

PATENT NO. : 7,254,850 B2  Page 1 of 1
APPLICATION NO. : 11/422365
DATED : August 14, 2007
INVENTOR(S) : Newkirk et al.

It is certified that error appears in the above-identified patent and that said Letters Patent is hereby corrected as shown below:

Claim 3, Column 10, Line 47: "cater" should be -- carrier --

Claim 3, Column 10, Line 50: "cater" should be -- carrier --

Claim 15, Column 12, Line 2: "bead" should be -- head --

Signed and Sealed this

Twenty-third Day of December, 2008

JON W. DUDAS
*Director of the United States Patent and Trademark Office*